United States Patent
Pennings et al.

(10) Patent No.: US 9,790,545 B2
(45) Date of Patent: Oct. 17, 2017

(54) METHOD FOR DETERMINING THE NEURODEVELOPMENTAL TOXICITY OF A COMPOUND IN VITRO

(71) Applicants: UNIVERSITEIT MAASTRICHT, Maastricht (NL); Academisch Ziekenhuis Maastricht, Maastricht (NL); Rijksinstituut Voor Volksgezondheid en Milieu, Bilthoven (NL)

(72) Inventors: Jeroen Lambertus Antonius Pennings, Bilthoven (NL); Petrus Theodorus Theunissen, Bilthoven (NL); Aldert Henrick Piersma, Bilthoven (NL)

(73) Assignees: UNIVERSITEIT MAASTRICHT, Maastricht (NL); ACADEMISCH ZIEKENHUIS MAASTRICHT, Maastricht (NL)

( * ) Notice: Subject to any disclaimer, the term of this patent is extended or adjusted under 35 U.S.C. 154(b) by 769 days.

(21) Appl. No.: 13/864,778

(22) Filed: Apr. 17, 2013

(65) Prior Publication Data

US 2013/0316924 A1 Nov. 28, 2013

(30) Foreign Application Priority Data

Apr. 17, 2012 (EP) .................................... 12164410

(51) Int. Cl.
*C12Q 1/68* (2006.01)
(52) U.S. Cl.
CPC ......... *C12Q 1/6837* (2013.01); *C12Q 1/6876* (2013.01); *C12Q 2600/142* (2013.01)
(58) Field of Classification Search
None
See application file for complete search history.

(56) References Cited

PUBLICATIONS

Theunissen Peter T et al: "Transcriptomic Concentration-Response Evaluation of Valproic Acid Cyproconazole and Hexaconazole in the Neural Embryonic Stem Cell Test (ESTn)," Toxicological Sciences, Academic Press, San Diego. FL. US. vol. 125, No. 2, Feb. 1, 2012 (Feb. 1, 2012), pp. 430-438.
Nagano Reiko et al: "Multi-parametric profiling network based on gene expression and phenotype data: a novel approach to developmental neurotoxicity testing," International Journal of Molecular Sciences, vol. 13, No. 1, Dec. 23, 2011 (Dec. 23, 2011), pp. 187-207.
Stummann T C et al: "Hazard assessment of methylmercury toxicity to neuronal induction in embryogenesis using human embryonic stem cells," Toxicology, vol. 257, No. 3, Mar. 29, 2009 (Mar. 29, 2009), pp. 117-126.
Pennings Jeroen L A et al: "An optimized gene set for transcriptomics based neurodevelopmental toxicity prediction in the neural embryonic stem cell test," Toxicology, vol. 300, No. 3, Oct. 28, 2012 (Oct. 28, 2012), pp. 158-167.
European Search Report, EP 12164410.8, dated Sep. 3, 2012.

*Primary Examiner* — Celine Qian
(74) *Attorney, Agent, or Firm* — TraskBritt, P.C.

(57) ABSTRACT

This invention is in the field of medical molecular diagnostics. It provides methods and means for the in vitro detection of the neurodevelopmental toxicity of a compound by determining the gene expression of a limited number of genes. More in particular, it relates to a method for determining the likelihood that a compound is neurodevelopmental toxic, comprising the steps of: providing embryonic stem cells, allowing the stem cells to form embryoid bodies, allowing the embryoid bodies to differentiate into neural cells, in the presence of said compound, thereby creating a neural differentiation culture, extracting total RNA from the cells in said neural differentiation culture, determining the expression levels of genes Hoxb6, Nrk, 1700011H14Rik and Tph1, comparing the expression levels with a predetermined reference value and determining the increase or decrease of the expression level relative to the reference value, wherein a relative increase or decrease in expression value of more than 20% indicates that a compound is neurodevelopmental toxic.

7 Claims, No Drawings

METHOD FOR DETERMINING THE NEURODEVELOPMENTAL TOXICITY OF A COMPOUND IN VITRO

CROSS-REFERENCE TO RELATED APPLICATIONS

This application claims the benefit under the Paris Convention to EP 12164410.8 filed Apr. 17, 2012, the disclosure of which is hereby incorporated herein in its entirety by this reference.

FIELD OF THE INVENTION

This invention is in the field of medical molecular diagnostics. It provides methods and means for the in vitro detection of the neurodevelopmental toxicity of a compound by determining the gene expression of a limited number of genes.

BACKGROUND OF THE INVENTION

Current chemical hazard assessment for developmental toxicity is built upon globally harmonized OECD (Organization for Economic Co-operation and Development) animal test guidelines, providing a structure for chemical risk assessment and in addition encouraging the development of alternative testing strategies. Under REACH (Regulation, Evaluation and Authorization of Chemicals) guidelines, ~60% of all animals will be used for reproductive and developmental toxicity studies (van der Jagt et al., 2004).

In order to reduce the number of experimental animals needed for developmental toxicity testing, cell based alternative test methods are being developed, such as, embryonic stem cell tests studying multiple differentiation lineages (Genschow et al., 2004; Piersma et al., 2004; Theunissen et al., 2010; zur Nieden et al., 2010), the whole embryo culture (WEC) (Piersma et al., 2004) and the zebrafish embryo test (Hermsen et al., 2011; Nagel, 2002).

An important target for developmental toxicity is the developing nervous system. Classical developmental toxicants, such as, methylmercury (MeHg), valproic acid, cyproconazole and ethanol particularly target neural development resulting in neural tube defects, craniofacial malformations, mental retardation and fetal alcohol syndrome (Alsdorf and Wyszynski, 2005; Faustman et al., 2002; Welch-Carre, 2005).

Current in vitro test systems for determining neurodevelopmental toxicity depend on assessing cellular endpoints of toxicity, such as, cell morphology (neural outgrowth, cytotoxicity, migration) (Mundy et al., 2010; Radio and Mundy, 2008) or functional parameters determined by electric conductivity (Shafer et al., 2002).

Regulatory authorities often require that compounds are tested in animals for neurodevelopmental toxicity. Such systems suffer from the disadvantage that they are laborious and costly and require large numbers of animals. In addition, the methods involve behavioral testing which is inherently variable and requires substantial efforts and experimental skills, presupposing high investments in training and equipment.

Prediction of neurodevelopmental toxicity by in vitro methods is hampered by the various mechanisms through which the toxicity can occur. We previously showed that the differentiation track algorithm can be applied to predict toxicity in the neural stem cell test (Theunissen et al., Toxicol Sci. 2011 August; 122(2):437-47). This algorithm relates gene expression changes due to compound exposure at a given time point to gene expression changes to an earlier and later time point by "normal" (unexposed) differentiation. However, until now this relied on using over a thousand genes, and no small and optimized set was available.

It is an object of the present invention to overcome or ameliorate at least some of the disadvantages of the prior art methods.

SUMMARY OF THE INVENTION

It was found that the neurodevelopmental toxicity of a compound could be determined by analyzing the expression level of genes Hoxb6, Nrk, 1700011H14Rik and Tph1.

The invention therefore relates to a method for determining the likelihood that a compound is neurodevelopmental toxic, comprising the steps of:
a. Providing embryonic stem cells,
b. Allowing the stem cells to form embryoid bodies,
c. Allowing the embryoid bodies to differentiate into neural cells, in the presence of said compound, thereby creating a neural differentiation culture,
d. Extracting total RNA from the cells in said neural differentiation culture,
e. Determining the expression levels of genes Hoxb6, Nrk, 1700011H14Rik and Tph1,
f. Comparing the expression levels with a predetermined reference value and determining the increase or decrease of the expression level relative to the reference value, wherein a relative increase or decrease in expression value of more than 20% indicates that a compound is neurodevelopmental toxic.

DETAILED DESCRIPTION OF THE INVENTION

The present study provides an analysis of differential gene expression in the presence of neurodevelopmental toxicants. This appeared to provide a robust method to monitor neural differentiation in an vitro system wherein embryonic stem cells are allowed to differentiate into neural cells.

The invention therefore relates to a method for determining the likelihood that a compound is neurodevelopmental toxic, comprising the steps of:
a. Providing embryonic stem cells,
b. Allowing the stem cells to form embryoid bodies,
c. Allowing the embryoid bodies to differentiate into neural cells, in the presence of said compound, thereby creating a neural differentiation culture,
d. Extracting total RNA from the cells in said neural differentiation culture,
e. Determining the expression levels of genes Hoxb6, Nrk, 1700011H14Rik and Tph1,
f. Comparing the expression levels with a predetermined reference value and determining the increase or decrease of the expression level relative to the reference value, wherein a relative increase or decrease in expression value of more than 20% indicates that a compound is neurodevelopmental toxic.

The method employs a cell culture assay based on embryonic stem cells. In the examples section we used ES-D3 mouse embryonic stem cells (ESC) obtained from ATCC, Rockville, Md., USA, cultured as detailed in example 2. Any embryonic stem cell culture may be employed in the method according to the invention. A skilled person will know how to adapt the presently exemplified methods to the use of other suitable embryonic stem cell cultures so that it will yield good results in the method according to the invention.

The term "embryonic stem cells," as used herein, relates to cells capable of differentiation into diverse specialized cell types that may be isolated from the inner cell mass of blastocysts.

The term "neurodevelopmental toxic" refers to the property of a chemical substance to interfere with the development of neural cells or structures during prenatal development in vertebrates. Disorders considered to be neurodevelopmental in origin or to have neurodevelopmental consequences when they occur in infancy and childhood include autism and autism spectrum disorders, such as, Asperger syndrome, traumatic brain injury (including congenital injuries, such as, those that cause cerebral palsy, communication, speech and language disorders), genetic disorders, such as, fragile-X syndrome, and Down syndrome. Neurodevelopmental disorders are associated with widely varying degrees of mental, emotional, physical and economic burden to individuals, families and society in general.

The term "genes Hoxb6, Nrk, 1700011H14Rik and Tph1," is used herein, to refer to genes homeobox B6, Nik related kinase, RIKEN cDNA 170001H14 and tryptophan hydrolase 1, and their homologs in other species.

The term "expression levels," is used herein, to mean the level of expression of messenger RNA from a gene. It may be determined by methods, such as, microarray, real-time PCR or other methods known in the art.

Calculating p-values using the differentiation track algorithm can be performed in statistical software, such as, R, Splus or other software available to a skilled person.

The term "relative expression levels" or "relative expression values," is used herein, to mean the ratio of the expression level of any of the genes Hoxb6, Nrk, 1700011H14Rik and Tph1 and a reference expression value.

The term "reference value" refers to an expression level of a certain gene when not exposed to a neurodevelopmental toxic compound. Reference values are preferably determined per gene. Reference values for the expression levels of a gene when not exposed to a developmentally toxic compound may be obtained by performing a method as described above without contacting the embryo with a compound. Reference values may also be obtained by performing the method according to the invention with a known non-developmental toxic compound. It is preferred to use a reference value obtained without contacting the embryo with a compound.

The term "a relative increase or decrease in expression value of more than 20%" is used to mean "a relative increase or decrease in expression value of more than 22%, 24%, 26%, 28%, 30%, 32%, 34%, 36%, 38%, 40%, 45%, 50% or more.

When murine embryonic stem cells (ESC) were used in the method according to the invention, it was found to be advantageous to allow the stem cells to form embryoid bodies for about 3 days before contacting them with the compound. The invention therefore relates to a method as described above, wherein step c is carried out 3 days after the start of step b.

In the methods as exemplified herein, it was also found advantageous to allow the neural differentiation culture to grow for one day before isolating total RNA from the differentiating cells. The invention therefore also relates to a method as described above wherein step d is carried out 1 day after step c.

Also, it was found advantageous to calculate neurodevelopmental toxicity p-values by relating gene expression levels in compound-exposed neural differentiation cultures to gene expression levels at three different time points in unexposed cultures, i.e., the same time point (1 day after step c), the unexposed embryoid bodies (point c), and another day of unexposed culture (2 days after point c).

It was found most suitable to induce neural differentiation by incubating the embryoid bodies with a retinoid, preferably retinoic acid. The invention therefore also relates to a method as described above, wherein a retinoid, preferably retinoic acid is used for inducing the embryoid bodies to differentiate into neural cells, thereby establishing a neural differentiation culture.

Table 1 shows the results obtained when a method according to the invention was used to determine the neurodevelopmental toxicity of 19 different compounds.

TABLE 1 relative expression values of 4 different genes under the influence of 19 different compounds.

| | nr | | | | |
|---|---|---|---|---|---|
| symbol | 1 Hoxb6 | 2 Nrk | 3 1700011H14Rik | 4 Tph1 | Golden standard |
| cypL | 0.808 | 0.713 | 1.048 | 1.114 | nontox |
| hexL | 0.858 | 0.800 | 1.063 | 1.047 | nontox |
| hexH | 1.197 | 1.253 | 1.208 | 0.878 | nontox |
| VpaL | 0.807 | 0.914 | 0.962 | 0.944 | nontox |
| aceL | 0.917 | 0.909 | 1.175 | 0.891 | nontox |
| cbzL | 0.991 | 1.055 | 0.870 | 0.945 | nontox |
| fluL | 0.933 | 1.063 | 1.132 | 0.897 | nontox |
| mehpL | 0.920 | 0.859 | 0.988 | 0.955 | nontox |
| pengL | 0.896 | 1.113 | 0.928 | 0.988 | nontox |
| pengH | 0.884 | 0.936 | 1.073 | 0.888 | nontox |
| pheL | 0.839 | 0.766 | 1.146 | 0.817 | nontox |
| mehgH | 1.302 | 0.719 | 1.665 | 1.116 | tox |
| cypH | 1.134 | 1.312 | 1.289 | 1.137 | tox |
| VpaH | 0.721 | 1.518 | 0.316 | 1.130 | tox |
| aceH | 1.100 | 1.290 | 0.562 | 1.094 | tox |
| cbzH | 0.950 | 1.217 | 0.533 | 0.751 | tox |
| fluH | 1.200 | 1.208 | 1.792 | 0.809 | tox |
| mehpH | 0.742 | 0.748 | 0.914 | 0.759 | tox |
| pheH | 0.840 | 0.781 | 0.995 | 0.781 | tox |

A relative change in expression of 20% was found to be statistically significant.

The criteria for scoring a compound as developmental toxic may vary, depending on the specific requirements of the user. When a high sensitivity is required, a compound may be scored as neurodevelopmental toxic when at least one of the genes Hoxb6, Nrk, 1700011H14Rik and Tph1 showed a relative change in the expression value of more than 20%.

When a high specificity is required, a compound may be scored as neurodevelopmental toxic when at least three of the genes Hoxb6, Nrk, 1700011H14Rik and Tph1 showed a relative change in the expression value of more than 20%.

The method according to the invention provided particularly reliable results when a compound was scored as neurodevelopmental toxic when at least two of the genes Hoxb6, Nrk, 1700011H14Rik and Tph1 showed a relative change in the expression value of more than 20%.

In that case, the method according to the invention proved to be 100% sensitive and 91% specific. (Table 2).

Table 2 Sensitivity and specificity of a method according to the invention, wherein a compound was scored as neurodevelopmental toxic when at least 2 genes selected from the group of genes Hoxb6, Nrk, 1700011H14Rik and Tph1 showed a relative change in the expression value of more than 20%.

| Experimental outcome | TOX | NON TOX | Total |
|---|---|---|---|
| Golden standard | | | |
| TOX | 8 | 0 | 8 |
| NON TOX | 1 | 10 | 11 |
| Total | 9 | 10 | 19 |

The 19 test compounds employed in this study are shown in table 3.

TABLE 3 test compounds employed in this study

| Label | Exposure | Concentration (µM) | Neuro-developmentally toxic |
|---|---|---|---|
| mehgH | Methylmercury chloride | 0.025 | yes |
| cypL | Cyproconazole | 1.5 | no |
| cypH | Cyproconazole | 100 | yes |
| hexL | Hexaconazole | 0.4 | no |
| hexH | Hexaconazole | 25 | no |
| vpaL | Valproic acid | 15 | no |
| vpaH | Valproic acid | 1000 | yes |
| aceL | Acetaldehyde | 1 | no |
| aceH | Acetaldehyde | 30 | yes |
| cbzL | Carbamazepine | 3 | no |
| cbzH | Carbamazepine | 100 | yes |
| fluL | Flusilazole | 0.3 | no |
| fluH | Flusilazole | 10 | yes |
| mehpL | Monoethylhexylphtalate | 3 | no |
| mehpH | Monoethylhexylphtalate | 100 | yes |
| pengL | Penicillin G | 30 | no |
| pengH | Penicillin G | 1000 | no |
| pheL | Phenytoin | 1 | no |
| pheH | Phenytoin | 30 | yes |

The method as described above could even be further improved when at least one of the genes 5-9 from table 4 was also tested in the method according to the invention. Improved in this context means that the number of correctly predicted compounds increases or that the test becomes more robust, for example, due to the fact that the reproducibility or the accuracy or the reliability of the method improves.

TABLE 4

Genes useful in the method according to the invention.

| Number | GeneID | Symbol | Description |
|---|---|---|---|
| 1 | 67082 | 1700011H14Rik | RIKEN cDNA 1700011H14 gene |
| 2 | 15414 | Hoxb6 | homeobox B6 |
| 3 | 21990 | Tph1 | tryptophan hydroxylase 1 |
| 4 | 27206 | Nrk | Nik related kinase |
| 5 | 106042 | Prickle1 | prickle homolog 1 (*Drosophila*) |
| 6 | 219151 | Scara3 | scavenger receptor class A, member 3 |
| 7 | 21808 | Tgfb2 | transforming growth factor, beta 2 |
| 8 | 12903 | Crabp1 | cellular retinoic acid binding protein 1 |
| 9 | 15413 | Hoxb5 | homeobox B5 |

The invention therefore also relates to a method, as described above, wherein in addition to the expression of genes Hoxb6, Nrk, 1700011H14Rik and Tph1, the expression of at least one gene selected from the group consisting of Prickle1, Scara3, Tgfb2, Crabp1 and Hoxb5 is tested.

The method according to the invention is more reliable than prior art methods, easier to perform, cheaper, and yields results faster.

EXAMPLES

Example 1: Culture Media

Complete medium (CM) contained Dulbecco's modified eagle's medium (DMEM) (Gibco BRL, Gaithersburg, Md., USA) supplemented with 20% fetal bovine serum (Hyclone, Logan, Utah, USA), 1% nonessential amino acids (Gibco BRL, Gaithersburg, Md., USA), 1% penicillin/streptomycin (Gibco BRL, Gaithersburg, Md., USA), 2 mM L-glutamine (Gibco BRL, Gaithersburg, Md., USA) and 0.1 mM â-mercapto ethanol (Sigma-Aldrich, Zwijndrecht, The Netherlands). Low serum medium (LS), had the same composition as CM except that the serum percentage is 10%. Insulin-transferrin-selenite-fibronectin medium (ITS) contained DMEM/Ham's nutrient mixture F12 (DMEM/F12) medium (Gibco, BRL, Gaithersburg, Md., USA) supplemented with 0.2 ug/ml bovine insulin (Sigma-Aldrich, Zwijndrecht, The Netherlands), 1% Penicillin/streptomycin (Gibco BRL, Gaithersburg, Md., USA), 2 mM L-glutamine (Gibco BRL, Gaithersburg, Md., USA), 30 nM sodium selenite (Sigma-Aldrich, Zwijndrecht, The Netherlands), 50 µg/ml apo-transferrin (Sigma-Aldrich, Zwijndrecht, The Netherlands) and 2.5 ug/ml fibronectin (Invitrogen, Carlsbad, Calif., USA). N2 medium contained DMEM/F12 medium (Gibco, BRL, Gaithersburg, Md., USA) supplemented with 0.2 ug/ml bovine insulin (Sigma-Aldrich, Zwijndrecht, The Netherlands), 1% penicillin/streptomycin (Gibco BRL, Gaithersburg, Md., USA), 30 nM sodium selenite (Sigma-Aldrich, Zwijndrecht, The Netherlands), 50 µg/ml apo-transferrin (Sigma-Aldrich, Zwijndrecht, The Netherlands).

Example 2: Embryonic Stem Cell Culture

Murine embryonic stem cells (ESC) (ES-D3, ATCC, Rockville, Md., USA) were routinely subcultured every 2-3 days and grown as a monolayer in CM supplemented with leukemia inhibiting factor (LIF) (Chemicon, Temecula, Calif., USA) at a final concentration of 1000 units/ml. The cells were maintained in a humidified atmosphere at 37° C. and 5% CO2.

Example 3: Neural Differentiation Culture

Differentiation of ESC into the neural lineage was carried out as described earlier (Theunissen et al., 2010). In brief, stem cell suspensions (3.75×104 cells/ml) were placed on ice before the initiation of the culture. Drops (20 µl) containing 750 cells in CM were placed onto the inner side of the lid of a 90 cm Petri dish filled with phosphate-buffered saline (PBS) (Gibco BRL, Gaithersburg, Md.) and incubated at 37° C., 90% relative humidity and 5% CO2. After 3 days of hanging drop culture embryoid bodies (EB) had formed and were subsequently transferred to 60 mm bacterial Petri dishes (Greiner Bio-one, Frickenhausen, Germany) containing CM supplemented with 0.5 µM retinoic acid (RA). On day 5, EB were plated on laminin (Roche, Basel, Switzerland) coated dishes (Corning Incorporated, Corning, N.Y., USA) in LS medium supplemented with 2.5 ug/ml fibronectin (Invitrogen, Carlsbad, Calif., USA). One day later, on day 6, the LS medium was replaced by ITS medium. On day 7, EB were washed with phosphate buffered saline (PBS) (Gibco BRL, Gaithersburg, Md., USA) and incubated in cell dissociation buffer (Gibco BRL, Gaithersburg, Md., USA) for 3 minutes. Then EB were carefully detached from each Petri dish without dissociating the EBs and the entire content was replated on poly-L-ornithine (Sigma-Aldrich, Zwijndrecht, The Netherlands) and laminin coated dish in N2 medium supplemented with 10 ng/ml basic fibroblast growth factor (bFGF) (Srtathmann-Biotec AG, Englewood, Colo., USA). The N2 medium supplemented with bFGF was replaced every other day for 7 days.

Example 4: Treatment and Morphological Scoring for Effects on Neural Outgrowth Methylmercury chloride (MeHg) (CAS number 115-09-3, Sigma-Aldrich, Zwijndrecht, The Netherlands) was diluted in DMSO and added to the medium to final concentrations in culture of 25 nM MeHg.

Cyproconazole (CAS number 94361-06-5, Sigma-Aldrich, Zwijndrecht, The Netherlands) was diluted in DMSO and added to the medium to final concentrations in culture of 1.5 or 100 µM cyproconazole.

Hexaconazole (HEX) (CAS number 79983-71-4, Sigma-Aldrich, Zwijndrecht, The Netherlands) was diluted in DMSO and added to the medium to final concentrations in culture of 0.4 or 25 µM hexaconazole.

Valproic acid sodium salt (VPA) (CAS number 1069-66-5, Sigma-Aldrich, Zwijndrecht, The Netherlands) was diluted in DMSO and added to the medium to final concentrations in culture of 15 or 1000 µM valproic acid.

Acetaldehyde (ACE) (CAS number 75-07-0, Sigma-Aldrich, Zwijndrecht, The Netherlands), was diluted in DMSO and added to the medium to final concentrations in culture of 1 or 30 µM acetaldehyde.

Carbamazepine (CBZ) (CAS number 298-46-4, Sigma-Aldrich, Zwijndrecht, The Netherlands), was diluted in DMSO and added to the medium to final concentrations in culture of 3 or 100 µM carbamazepine.

Flusilazole (FLU) (CAS number 85509-19-9, Sigma-Aldrich, Zwijndrecht, The Netherlands), was diluted in DMSO and added to the medium to final concentrations in culture of 0.3 or 10 µM flusilazole.

Monoethylhexylphthalate (MEHP) (CAS number 4376-20-9), Wako Chemicals GmbH, Neuss, Germany), was diluted in DMSO and added to the medium to final concentrations in culture of 3 or 100 µM Monoethylhexylphthalate.

Penicillin G (PENG) (CAS number 69-57-8, Sigma-Aldrich, Zwijndrecht, The Netherlands) was diluted in DMSO and added to the medium to final concentrations in culture of 30 or 1000 µM Penicilin G.

Phenytoin (PHE) (CAS number 57-41-0, Sigma-Aldrich, Zwijndrecht, The Netherlands) was diluted in DMSO and added to the medium to final concentrations in culture of 1 or 30 µM phenytoin.

Control EB were treated with 0.01% DMSO as described earlier from day 3 of the protocol until day 11 (Theunissen et al., 2010). Effects were determined by assessing of the morphological extent of neural outgrowth, at day 11, observed using an IX51 inverted microscope (Olympus, Zoeterwoude, The Netherlands) with CellD software (Olympus, Zoeterwoude, The Netherlands). Morphological neural outgrowth was scored as <75% or =75% of the neural corona surrounding each EB, irrespective of the distance of outgrowth from the EB. Parallel cultures were harvested for gene expression analysis at earlier time points.

Example 5: RNA Isolation and Whole-Genome Expression Profiling

Control differentiation cultures were harvested on culture days 3, 4 and 5 (8 replicates per group). Differentiation cultures were exposed to the neurodevelopmental toxicants and controls from day 3 onwards and harvested on day 4 (24 h exposure) (8 replicates per group). Cells (~40-50 EB/sample) were directly collected in RNA Protect (Qiagen Benelux, Venlo, The Netherlands) to stabilize RNA, and total RNA was purified using the Qiagen RNEasy Plus Mini Kit (Qiagen Benelux, Venlo, The Netherlands) following the manufacturer's instructions. RNA quantity was determined using the NanoDrop Spectophotometer (Isogen Lifescience, de Meern, The Netherlands). RNA integrity was assessed on the 2100 Bioanalyzer (Agilent, Santa Clara, Calif., USA) using the RNA 6000 Nano Chip Kit (Agilent, Santa Clara, Calif., USA), and good quality RNA was used for gene expression analysis (RNA integrity number (RIN)>8.0). Labeled aRNA target was generated by using the Affymetrix genechip (Affymetrix, Santa Clara, Calif., US) (3'IVT express kit 4×24 reactions (P/N 901225) according to the instructions in the user manual. Briefly, 250 ng of each total RNA sample and also controls were used to prepare first-strand cDNA. After making the complementary second strand, the double stranded cDNA is amplified by in vitro transcription (IVT). During this IVT reaction a biotinylated nucleotide analog is incorporated in the aRNA. This IVT reaction was followed by aRNA purification with magnetic beads and fragmentation (15 µg) of each aRNA sample. The whole process from first-strand cDNA synthesis till fragmentation of the aRNA was performed by the Xiril Neon 150 robotic system (GC-Biotech, Alphen aan den Rijn, The Netherlands).

After fragmentation, a 250 µl hybridization cocktail with 12.5 µg of fragmented aRNA was prepared. 200 µl of this cocktail (10 µg aRNA target) was applied to the Mouse Genome 430 2.0 arrays (P/N 900497, Affymetrix, Santa Clara, Calif., US) and hybridized for 16 hours at 45° C. in a Genechip Hybridization Oven 640. After hybridization the arrays were washed and stained with a Genechip Fluidics Station 450 using the Affymetrix genechip hybridization wash and stain kit (P/N 900720). Washed and stained arrays were scanned using the genechip scanner 3000 from Affymetrix. Hybridization was performed at Affymetrix (Santa Clara, Calif., US).

Example 6: Predicting Neurodevelopmental Toxicity

Statistical calculations used in this study were performed in R (worldwide web r-project.org). The algorithm for calculating p-values for differentiation track deviation is a described in (Theunissen et al., Toxicol Sci. 2011 122:437-47, Van Dartel, 2010a). Normalized gene expression data for a set of genes are log-transformed, and data for unexposed samples at 0 h, 24 h, and 48 h, together with compound treatment samples at 24 h, are used in a PCA. Coordinates along the first and second principal component are calculated for each sample. P-values for deviation of the 24 h compound-exposed samples from the differentiation track are determined by applying a Hotelling T-test to these coordinates compared to those of the 24 h control cultures.

REFERENCES

Van der Jagt, K., Tørsløv, J. and de Bruijn, J. (2004). Alternative approaches can reduce the use of test animals under REACH., Ed.^ Eds.). European Commission Report.

Genschow, E., Spielmann, H., Scholz, G., Pohl, I., Seiler, A., Clemann, N., Bremer, S. and Becker, K. (2004). Validation of the embryonic stem cell test in the international ECVAM validation study on three in vitro embryotoxicity tests. Altern Lab Anim 32, 209-44.

Piersma, A. H., Genschow, E., Verhoef, A., Spanjersberg, M. Q., Brown, N. A., Brady, M., Burns, A., Clemann, N., Seiler, A. and Spielmann, H. (2004). Validation of the postimplantation rat whole-embryo culture test in the international ECVAM validation study on three in vitro embryotoxicity tests. Altern Lab Anim 32, 275-307.

Theunissen, P. T., Schulpen, S. H., van Dartel, D. A., Hermsen, S. A., van Schooten, F. J. and Piersma, A. H. (2010). An abbreviated protocol for multilineage neural differentiation of murine embryonic stem cells and its perturbation by methyl mercury. Reprod Toxicol 29, 383-92, zur Nieden, N. I., Davis, L. A. and Rancourt, D. E. (2010). Comparing three novel endpoints for developmental osteotoxicity in the embryonic stem cell test. Toxicol Appl Pharmacol 247, 91-7, Hermsen, S. A., van den Brandhof, E. J., van der Ven, L. T. and Piersma, A. H. (2011). Relative embryotoxicity of two classes of chemicals in a modified zebrafish embryotoxicity test and comparison with their in vivo potencies. Toxicol In vitro, Nagel, R. (2002). DarT: The embryo test with the Zebrafish Danio rerio-a general model in ecotoxicology and toxicology. ALTEX 19 Suppl 1, 38-48.

Alsdorf, R. and Wyszynski, D. F. (2005). Teratogenicity of sodium valproate. Expert Opin Drug Saf 4, 345-53,].

Faustman, E. M., Ponce, R. A., Ou, Y. C., Mendoza, M. A., Lewandowski, T. and Kavanagh, T. (2002). Investigations of methylmercury-induced alterations in neurogenesis. Environ Health Perspect 110 Suppl 5, 859-64, Welch-Carre, E. (2005). The neurodevelopmental consequences of prenatal alcohol exposure. Adv Neonatal Care 5, 217-29, S1536-0903(05)00148-7 [pii] 10.1016/j.adnc.2005.04.007.

Costa, L. G., Fattori, V., Giordano, G. and Vitalone, A. (2007). An in vitro approach to assess the toxicity of certain food contaminants: methylmercury and polychlorinated biphenyls. Toxicology 237, 65-76, Shafer, T. J., Meacham, C. A. and Barone, S., Jr. (2002). Effects of prolonged exposure to nanomolar concentrations of methylmercury on voltage-sensitive sodium and calcium currents in PC12 cells. Brain Res Dev Brain Res 136, 151-64, Stummann, T. C., Hareng, L. and Bremer, S. (2007). Embryotoxicity hazard assessment of methylmercury and chromium using embryonic stem cells. Toxicology 242, 130-43, Walum, E. and Flint, O. P. (1990). Midbrain micromass cultures: a model for studies of teratogenic and subteratogenic effects on CNS development. Acta Physiol Scand Suppl 592, 61-72.

Bibel, M., Richter, J., Schrenk, K., Tucker, K. L., Staiger, V., Korte, M., Goetz, M. and Barde, Y. A. (2004). Differentiation of mouse embryonic stem cells into a defined neuronal lineage. Nat Neurosci 7, 1003-9, Okabe, S., Forsberg-Nilsson, K., Spiro, A. C., Segal, M. and McKay, R. D. (1996). Development of neuronal precursor cells and functional postmitotic neurons from embryonic stem cells in vitro. Mech Dev 59, 89-102, Mundy, W. R., Radio, N. M. and Freudenrich, T. M. (2010). Neuronal models for evaluation of proliferation in vitro using high content screening. Toxicology 270, 121-30, Radio, N. M. and Mundy, W. R. (2008). Developmental neurotoxicity testing in vitro: models for assessing chemical effects on neurite outgrowth. Neurotoxicology 29, 361-76, Robinson, J. F., Griffith, W. C., Yu, X., Hong, S., Kim, E. and Faustman, E. M. (2010a). Methylmercury induced toxicogenomic response in C57 and SWV mouse embryos undergoing neural tube closure. Reprod Toxicol 30, 284-91, Robinson, J. F., Guerrette, Z., Yu, X., Hong, S. and Faustman, E. M. (2010b). A systems-based approach to investigate dose- and time-dependent methylmercury-induced gene expression response in C57BL/6 mouse embryos undergoing neurulation. Birth Defects Res B Dev Reprod Toxicol 89, 188-200.

Robinson, J. F., van Beelen, V. A., Verhoef, A., Renkens, M. F., Luijten, M., van Herwijnen, M. H., Westerman, A., Pennings, J. L. and Piersma, A. H. (2010c). Embryotoxicant-specific transcriptomic responses in rat postimplantation whole-embryo culture. Toxicol Sci 118, 675-85, Krewski, D. (2007). Toxicity Testing in the Twenty-first Century (C. o. T. a. A. o. E. A. NRC, Ed.^ Eds.). National Academy of Sciences, Washington, D.C.

Nemeth, K. A., Singh, A. V. and Knudsen, T. B. (2005). Searching for biomarkers of developmental toxicity with microarrays: normal eye morphogenesis in rodent embryos. Toxicol Appl Pharmacol 206, 219-28, van Dartel, D. A., Pennings, J. L., de la Fonteyne, L. J., Brauers, K. J., Claessen, S., van Delft, J. H., Kleinjans, J. C. and Piersma, A. H. (2011). Evaluation of developmental toxicant identification using gene expression profiling in embryonic stem cell differentiation cultures. Toxicol Sci 119, 126-34, van Dartel, D. A., Pennings, J. L., de la Fonteyne, L. J., van Herwijnen, M. H., van Delft, J. H., van Schooten, F. J. and Piersma, A. H. (2010a). Monitoring developmental toxicity in the embryonic stem cell test using differential gene expression of differentiation-related genes. Toxicol Sci 116, 130-9, van Dartel, D. A., Pennings, J. L., van Schooten, F. J. and Piersma, A. H. (2010b). Transcriptomics-based identification of developmental toxicants through their interference with cardiomyocyte differentiation of embryonic stem cells. Toxicol Appl Pharmacol 243, 420-8, Cox, C., Clarkson, T. W., Marsh, D. O., Amin-Zaki, L., Tikriti, S. and Myers, G. G. (1989). Dose-response analysis of infants prenatally exposed to methyl mercury: an application of a single compartment model to single-strand hair analysis. Environ Res 49, 318-32.

Davidson, P. W., Myers, G. J. and Weiss, B. (2004). Mercury exposure and child development outcomes. Pediatrics 113, 1023-9.

Burbacher, T. M., Rodier, P. M. and Weiss, B. (1990). Methylmercury developmental neurotoxicity: a comparison of effects in humans and animals, Neurotoxicol Teratol 12, 191-202, Myers, G. J. and Davidson, P. W. (1998). Prenatal methylmercury exposure and children: neurologic, developmental, and behavioral research. Environ Health Perspect 106 Suppl 3, 841-7.

Irizarry, R. A., Hobbs, B., Collin, F., Beazer-Barclay, Y. D., Antonellis, K. J., Scherf, U. and Speed, T. P. (2003).

Exploration, normalization, and summaries of high density oligonucleotide array probe level data. Biostatistics 4, 249-64, Bolstad, B. M., Irizarry, R. A., Astrand, M. and Speed, T. P. (2003). A comparison of normalization methods for high density oligonucleotide array data based on variance and bias. Bioinformatics 19, 185-93.

de Leeuw, W. C., Rauwerda, H., Jonker, M. J. and Breit, T. M. (2008). Salvaging Affymetrix probes after probe-level re-annotation. BMC Res Notes 1, 66, Dai, M., Wang, P., Boyd, A. D., Kostov, G., Athey, B., Jones, E. G., Bunney, W. E., Myers, R. M., Speed, T. P., Akil, H., Watson, S. J. and Meng, F. (2005). Evolving gene/transcript definitions significantly alter the interpretation of GeneChip data. Nucleic Acids Res 33, Huang da, W., Sherman, B. T., Tan, Q., Collins, J. R., Alvord, W. G., Roayaei, J., Stephens, R., Baseler, M. W., Lane, H. C. and Lempicki, R. A. (2007). The DAVID Gene Functional Classification Tool: a novel biological module-centric algorithm to functionally analyze large gene lists. Genome Biol 8, R183, Boorsma, A., Foat, B. C., Vis, D., Klis, F. and Bussemaker, H. J. (2005). T-profiler: scoring the activity of predefined groups of genes using gene expression data. Nucleic Acids Res 33, Kuegler, P. B., Zimmer, B., Waldmann, T., Baudis, B., Ilmjarv, S., Hescheler, J., Gaughwin, P., Brundin, P., Mundy, W., Bal-Price, A. K., Schrattenholz, A., Krause, K. H., van Thriel, C., Rao, M. S., Kadereit, S. and Leist, M. (2010). Markers of murine embryonic and neural stem cells, neurons and astrocytes: reference points for developmental neurotoxicity testing. ALTEX 27, 17-42.

Su, A. I., Wiltshire, T., Batalov, S., Lapp, H., Ching, K. A., Block, D., Zhang, J., Soden, R., Hayakawa, M., Kreiman, G., Cooke, M. P., Walker, J. R. and Hogenesch, J. B. (2004). A gene atlas of the mouse and human protein-encoding transcriptomes. Proc Natl Acad Sci USA 101, Pearson, K. (1901). On lines and planes of closest fit to systems of points in space. Philos. Mag. 2, 559-72.

Niwa, H., Miyazaki, J. and Smith, A. G. (2000). Quantitative expression of Oct-3/4 defines differentiation, dedifferentiation or self-renewal of ES cells. Nat Genet 24, 372-6, Ogawa, K., Saito, A., Matsui, H., Suzuki, H., Ohtsuka, S., Shimosato, D., Morishita, Y., Watabe, T., Niwa, H. and Miyazono, K. (2007). Activin-Nodal signaling is involved in propagation of mouse embryonic stem cells. J Cell Sci 120, 55-65, Liu, L., Geisert, E. E., Frankfurter, A., Spano, A. J., Jiang, C. X., Yue, J., Dragatsis, I. and Goldowitz, D. (2007). A transgenic mouse class-III beta tubulin reporter using yellow fluorescent protein. Genesis 45, 560-9.

Moskowitz, P. F. and Oblinger, M. M. (1995). Transcriptional and post-transcriptional mechanisms regulating neurofilament and tubulin gene expression during normal development of the rat brain. Brain Res Mol Brain Res 30, 211-22, Abu-Abed, S., Dolle, P., Metzger, D., Beckett, B., Chambon, P. and Petkovich, M. (2001). The retinoic acid-metabolizing enzyme, CYP26A1, is essential for normal hindbrain patterning, vertebral identity, and development of posterior structures. Genes Dev 15, 226-40.

Abranches, E., Silva, M., Pradier, L., Schulz, H., Hummel, O., Henrique, D. and Bekman, E. (2009). Neural differentiation of embryonic stem cells in vitro: a road map to neurogenesis in the embryo. PLoS One 4, e6286, 10.

Kim, M., Habiba, A., Doherty, J. M., Mills, J. C., Mercer, R. W. and Huettner, J. E. (2009). Regulation of mouse embryonic stem cell neural differentiation by retinoic acid. Dev Biol 328, 456-71,]

Zimmer, B., Kuegler, P. B., Baudis, B., Genewsky, A., Tanavde, V., Koh, W., Tan, B., Waldmann, T., Kadereit, S. and Leist, M. (2010). Coordinated waves of gene expression during neuronal differentiation of embryonic stem cells as basis for novel approaches to developmental neurotoxicity testing. Cell Death Differ, cdd2010109 [pii]

Mitiku, N. and Baker, J. C. (2007). Genomic analysis of gastrulation and organogenesis in the mouse. Dev Cell 13, 897-907, Ceccatelli, S., Dare, E. and Moors, M. (2010). Methylmercury-induced neurotoxicity and apoptosis. Chem Biol Interact 188, 301-8, Spyker, J. M. and Smithberg, M. (1972). Effects of methylmercury on prenatal development in mice. Teratology 5, 181-90.

Pellizzer, C., Adler, S., Corvi, R., Hartung, T. and Bremer, S. (2004). Monitoring of teratogenic effects in vitro by analysing a selected gene expression pattern. Toxicol In vitro 18, 325-35, van Dartel, D. A., Pennings, J. L., Hendriksen, P. J., van Schooten, F. J. and Piersma, A. H. (2009). Early gene expression changes during embryonic stem cell differentiation into cardiomyocytes and their modulation by monobutyl phthalate. Reprod Toxicol 27, 93-102, Genschow, E., Spielmann, H., Scholz, G., Seiler, A., Brown, N., Piersma, A., Brady, M., Clemann, N., Huuskonen, H., Paillard, F., Bremer, S. and Becker, K. (2002). The ECVAM international validation study on in vitro embryotoxicity tests: results of the definitive phase and evaluation of prediction models. European Centre for the Validation of Alternative Methods. Altern Lab Anim 30, 151-76.

Theunissen P T, Pennings J L A, Robinson J F, Claessen S M H, Kleinjans J C S, Piersma A H. (2011) Time-response evaluation by transcriptomics of methylmercury effects on neural differentiation of murine embryonic stem cells. Toxicol Sci. August; 122(2):437-47.

What is claimed is:

1. A method for measuring the expression level of genes Hoxb6, Nrk, 1700011H14Rik, and Tph1, the method consisting essentially of:
   forming embryoid bodies,
   three days after forming embryoid bodies, differentiating the embryoid bodies into neural cells in the presence of a test compound thereby creating a neural differentiation culture,
   extracting total RNA from the cells after one day in the neural differentiation culture, and
   measuring the expression level of genes Hoxb6, Nrk, 1700011H14Rik, and Tph1 therein.

2. The method according to claim 1, further comprising measuring the expression level of at least one gene selected from the group consisting of Prickle1, Scara3, Tgfb2, Crabp1, and Hoxb5 in the total RNA.

3. The method according to claim 1, further comprising measuring the expression level of genes Prickle1, Scara3, Tgfb2, Crabp1, and Hoxb5 in the total RNA.

4. A method for measuring the expression level of genes Hoxb6, Nrk, 17000111H14Rik, and Tph1, the method comprising:
   forming embryoid bodies,
   differentiating the embryoid bodies into neural cells in the presence of a test compound thereby creating a neural differentiation culture, measuring the expression level of genes Hoxb6, Nrk, 1700011H1Rik, and Tph1 in the neural differentiation culture.

5. The method according to claim 4, further comprising measuring the expression level of at least one gene selected from the group consisting of Prickle1, Scara3, Tgro2, Crabp1, and Hoxb5 in the neural differentiation culture.

6. The method according to claim 4, wherein the expression levels are measured 1 day after differentiating embryoid bodies into neural cells.

7. The method according to claim 4, further comprising measuring the expression level of genes Prickle1, Scara3, Tgfb2, Crabp1, and Hoxb5 in the neural differentiation culture.

* * * * *